US010603189B1

(12) United States Patent
Higginbotham

(10) Patent No.: US 10,603,189 B1
(45) Date of Patent: Mar. 31, 2020

(54) DUAL PURPOSE PROSTHETIC FOOT SYSTEM AND METHOD OF USE

(71) Applicant: Darryl Scott Higginbotham, Allen, TX (US)

(72) Inventor: Darryl Scott Higginbotham, Allen, TX (US)

( * ) Notice: Subject to any disclaimer, the term of this patent is extended or adjusted under 35 U.S.C. 154(b) by 92 days.

(21) Appl. No.: 15/815,504

(22) Filed: Nov. 16, 2017

Related U.S. Application Data

(60) Provisional application No. 62/422,707, filed on Nov. 16, 2016.

(51) Int. Cl.
*A61F 2/66* (2006.01)
*A61F 2/80* (2006.01)

(52) U.S. Cl.
CPC .............. *A61F 2/6607* (2013.01); *A61F 2/80* (2013.01); *A61F 2002/6614* (2013.01)

(58) Field of Classification Search
CPC ........ A61F 2/604; A61F 2/6607; A61F 2/601; A61F 2/66; A61F 2/76; A61F 2/80; A61F 2002/6614; A61F 2002/6657; A61F 2002/5018
USPC ......................................... 623/27, 33, 47, 53
See application file for complete search history.

(56) References Cited

U.S. PATENT DOCUMENTS

| | | | | |
|---|---|---|---|---|
| 5,156,630 A | * | 10/1992 | Rappoport | A61F 2/6607 403/103 |
| 2004/0204770 A1 | * | 10/2004 | Curtis | A61F 2/5046 623/33 |
| 2008/0056814 A1 | * | 3/2008 | Klingenberg | B25B 31/005 403/322.2 |
| 2009/0082878 A1 | * | 3/2009 | Christensen | A61F 2/6607 623/55 |
| 2018/0271679 A1 | * | 9/2018 | Caldwell | A61F 2/60 |

* cited by examiner

*Primary Examiner* — Suba Ganesan
*Assistant Examiner* — Aren Patel
(74) *Attorney, Agent, or Firm* — Richard Eldredge

(57) ABSTRACT

A dual purpose prosthetic foot system enables a person to use the same prosthetic to either walk or swim. The foot part is joined at the ankle and can be locking in either a walking position or a swimming position. The foot allows common swimming equipment such as flippers to be attached.

4 Claims, 7 Drawing Sheets

DUAL PURPOSE PROSTHETIC FOOT SYSTEM AND METHOD OF USE

BACKGROUND

1. Field of the Invention

The present invention relates generally to prosthetics, and more specifically, to a prosthetic ankle system for simulating the function of the joint between a leg and a foot.

2. Description of Related Art

Prosthetic devices are well known in the art and are effective means to restore the functionality lost by missing a limb. For example, FIG. 1 depicts a conventional prosthetic ankle system 101 having a prosthetic leg 103 attached to a cushion 105 that is attached to a prosthetic foot 107. During use, the prosthetic leg 103 is attached to a user's stump 109. The leg 103 and foot 107 assist the user to walk and the impact of walking is lessened by the cushion 105.

One of the problems commonly associated with system 101 is its limited use. For example, the prosthetic foot 107 is attached to simulate walking however this position does not work well if the user were to go swimming which in turn would require removal of the prosthetic 101.

Accordingly, although great strides have been made in the area of prosthetic ankle systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
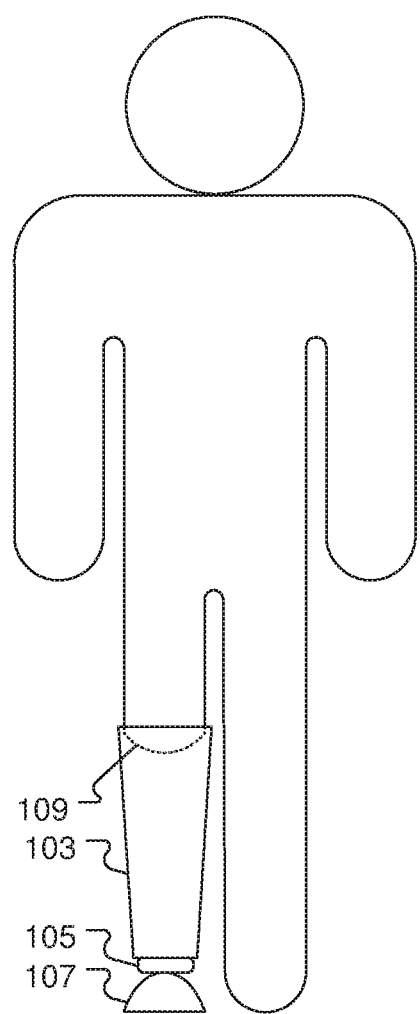
FIG. 1 is a front view of a common prosthetic ankle system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional prosthetic ankle systems. Specifically, the system of the present application enables a user to quickly change the position of the foot relative to the leg to facilitate either walking or swimming. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2A:
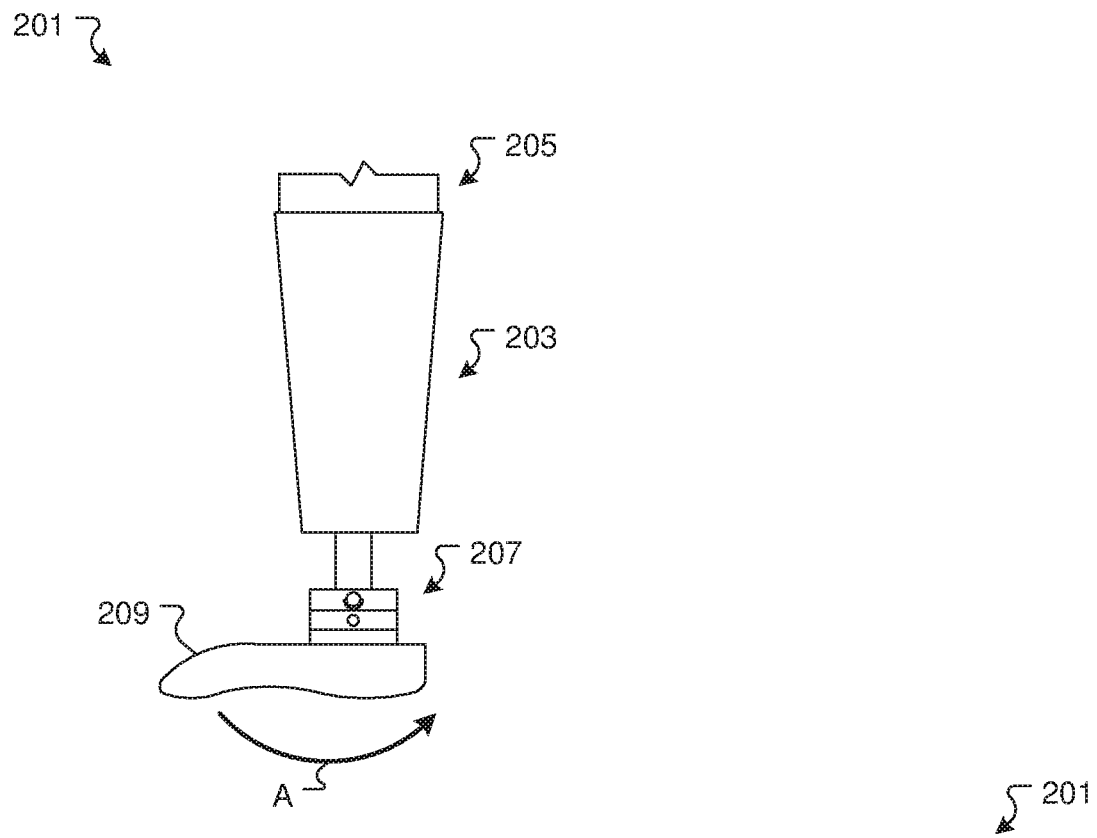
FIGS. 2A and 2B are side views of a dual purpose prosthetic foot system in accordance with a preferred embodiment of the present application.
Figure 2B:
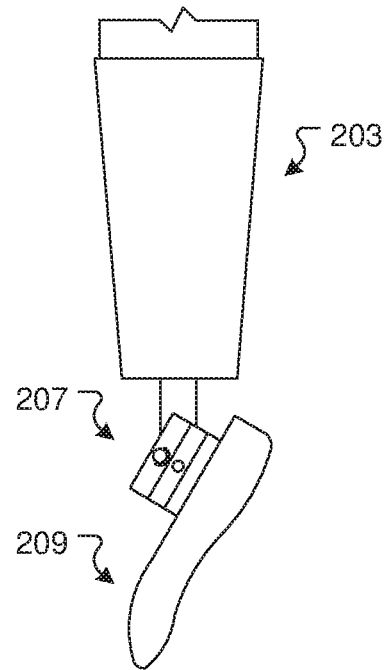

Referring now to the drawings wherein like reference characters identify corresponding or similar elements throughout the several views, FIGS. 2A and 2B depict side views of a dual purpose prosthetic foot system in accordance with a preferred embodiment of the present application. It will be appreciated that system 201 overcomes one or more of the above-listed problems commonly associated with conventional prosthetic ankle systems.

In the contemplated embodiment, system 201 includes a prosthetic leg 203 removably attached to a user's stump 205. The prosthetic leg 203 transfers the user's weight to a prosthetic foot 209 via ankle joint 207. Prosthetic leg 203 is rigidly attached to ankle joint 207 that enables the angle of the foot to change as depicted by motion A. The ankle joint 207 is rigidly attached to a prosthetic foot 209 that facilitates the user to stand or swim. In the contemplated embodiment the first position of the prosthetic foot 209 would be generally 90 degrees relative to the prosthetic leg 203. In the contemplated embodiment the second position of the prosthetic foot 209 would is between 115 degrees to 180 degrees relative to the prosthetic leg 203.

Figure 3:
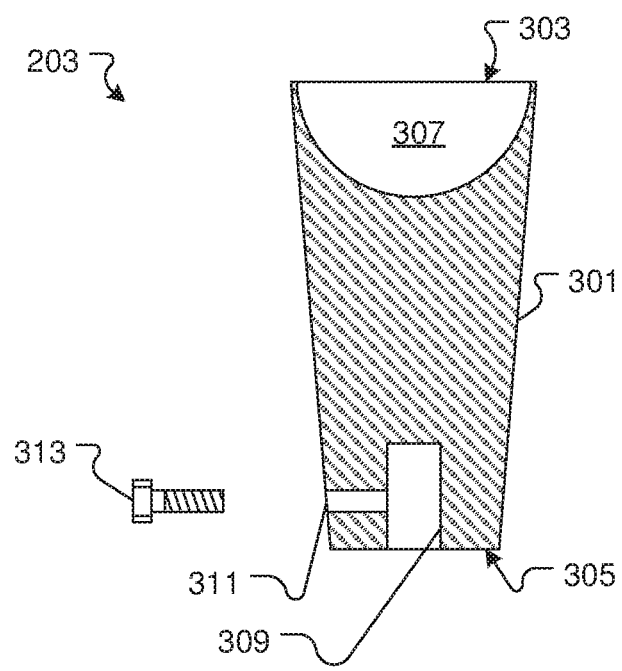
FIG. 3 is a side cross sectional view of the prosthetic leg of FIGS. 2A and 2B.

Referring now to FIG. 3, prosthetic leg 203 includes a leg body 301 with a top end 303 and a bottom end 305. A socket 307 extends inwardly from the top end 303. The socket rigidly attaches the prosthetic leg 203 to the user's stump 205. The bottom end 305 forms a cavity 309 that extends inwardly and attaches to the ankle joint 207 via a bolt 313 and a threaded hole 311 that extends through the thickness of leg body 301 to cavity 309.

Figure 4:
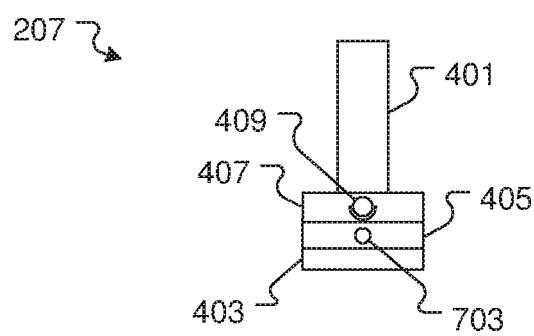
FIG. 4 is a side view of the ankle joint of FIGS. 2A and 2B.

Referring now to FIG. 4, ankle joint 207 includes a pylon 401 that attaches to prosthetic leg 203, a mating foot 403 that attaches to prosthetic foot 209, a pin plate 405 to fixedly attach pylon 401, a rotation plate 407 that determines the position of the mating foot 403 to the prosthetic leg 203 via pylon 401 and a pin 409.

Figure 5:
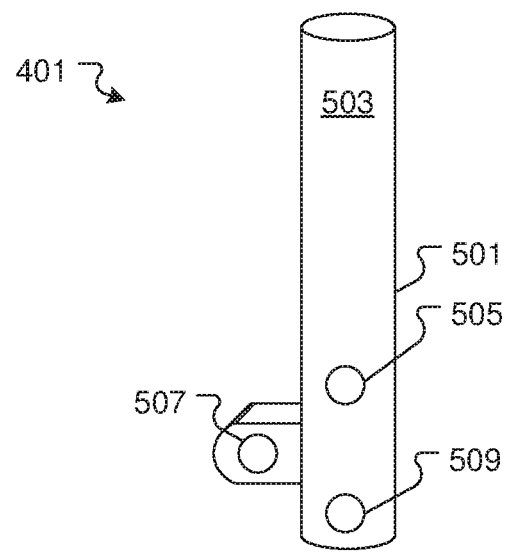
FIG. 5 is a perspective view of the pylon of FIG. 4.

Referring now to FIG. 5, pylon 401 comprises a tubular body 501 with surface 503 and two positioning holes 505, 507 that extends through the thickness of tubular body 501. Positioning holes 505 and 507 are on the same radius from a rotation hole 509. Tubular body 501 loose fits in cavity 309 and is fixedly attached there by tightening bolt 313 to apply force against the surface 503 of tubular body 501.

Figure 6:
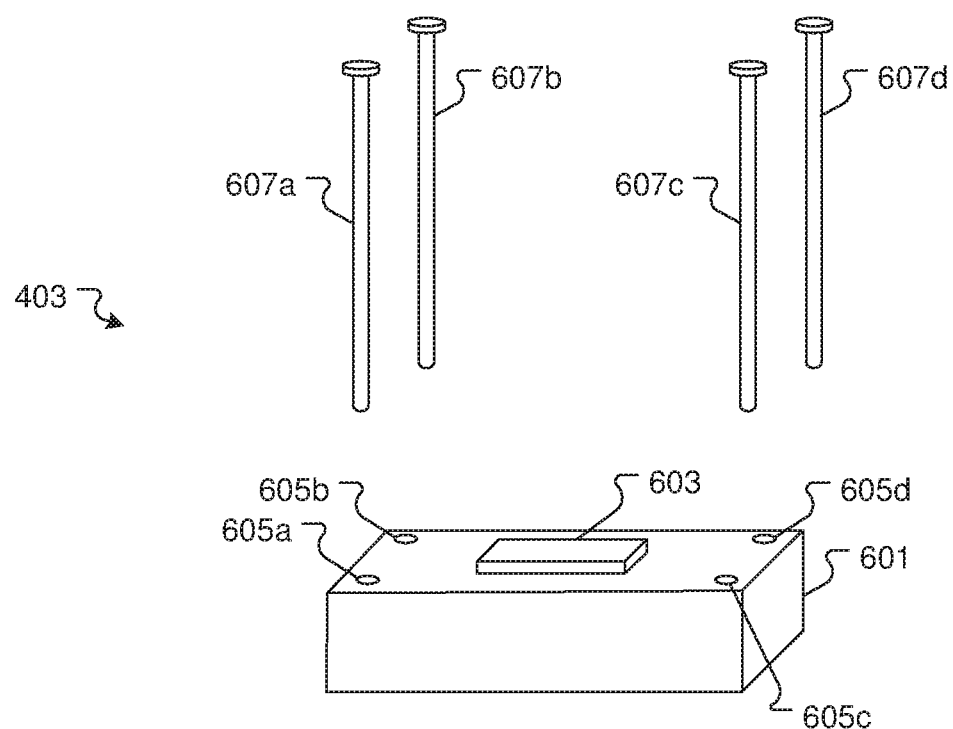
FIG. 6 is a perspective view of the mounting foot of FIG. 4.

Referring now to FIG. 6, mating foot 403 includes a mating body 601 that is rigidly attached to a wear plate 603 and has a plurality of holes 605 for a plurality of fasteners 607, which fasteners will fixedly attach the mating foot 403, pin plate 405, rotation plate 407 and the prosthetic foot 209 together. Wear plate 603 prevents damage to mating foot 403 from the movement of pylon 401.

Figure 7:
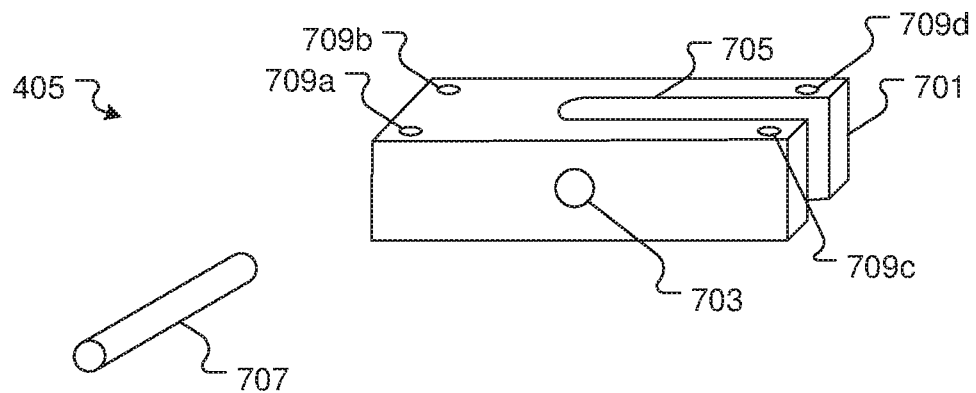
FIG. 7 is a perspective view of the pin plate of FIG. 4.
Figure 8:
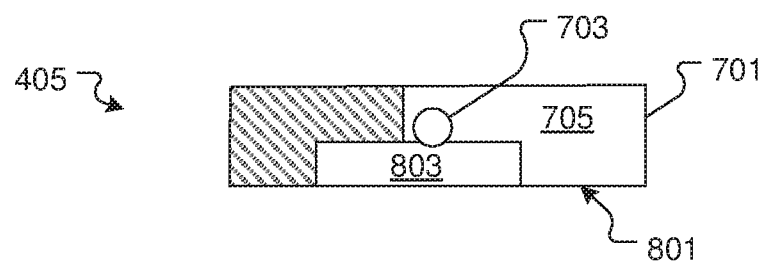
FIG. 8 is a side cross sectional view of the body of FIG. 7.

Referring now to FIGS. 7 and 8, pin plate 405 includes a first body 701 having bottom surface 801. A pin hole 703 passing through first body 701. A recess 803 on bottom surface 801 that fits over wear plate 603 and allows the bottom surface 801 of pin plate 403 to sit on mating body 601. A first slot 705 where the pylon 401 attaches to pin plate 405 and press fit pin 707 that is forced in pin hole 703 and freely enters rotation hole 509. First body 701 includes a plurality of holes 709a-d in line with and common to holes 605a-d to accept fasteners 607a-d.

Figure 9:
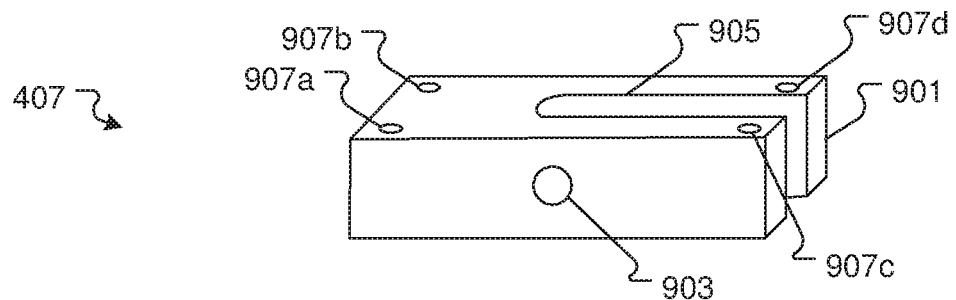
FIG. 9 is a perspective view of the rotation plate of FIG. 4.

Referring now to FIG. 9, rotation plate 407 includes a second body 901 having a position hole 903 passing through second body 901. The second body 901 has a second slot 905 where the pylon 401 has freedom of motion and a plurality of holes 907a-d in line with and common to holes 605a-d, 709a-d to accept fasteners 607a-d.

Figure 10:
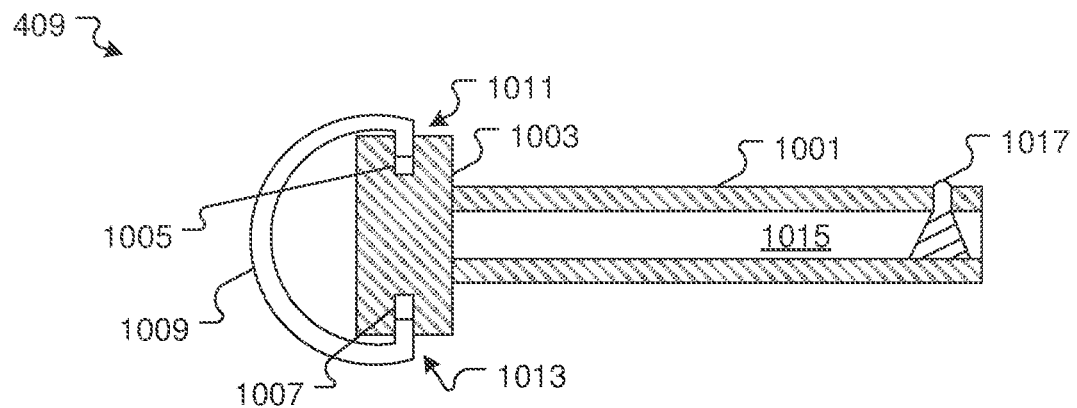
FIG. 10 is a side cross sectional view of the pin of FIG. 4.

Referring now to FIG. 10, pin 409 includes a hollow rod 1001 rigidly attached to a head 1003 that has two holes 1005, 1007 that pivotally attach a handle 1009 via a first end 1011 and second end 1013 of handle 1009. The empty space 1015 of hollow rod 1001 houses a retention device 1017 that keeps pin 409 in place in position hole 903.

Figure 11:
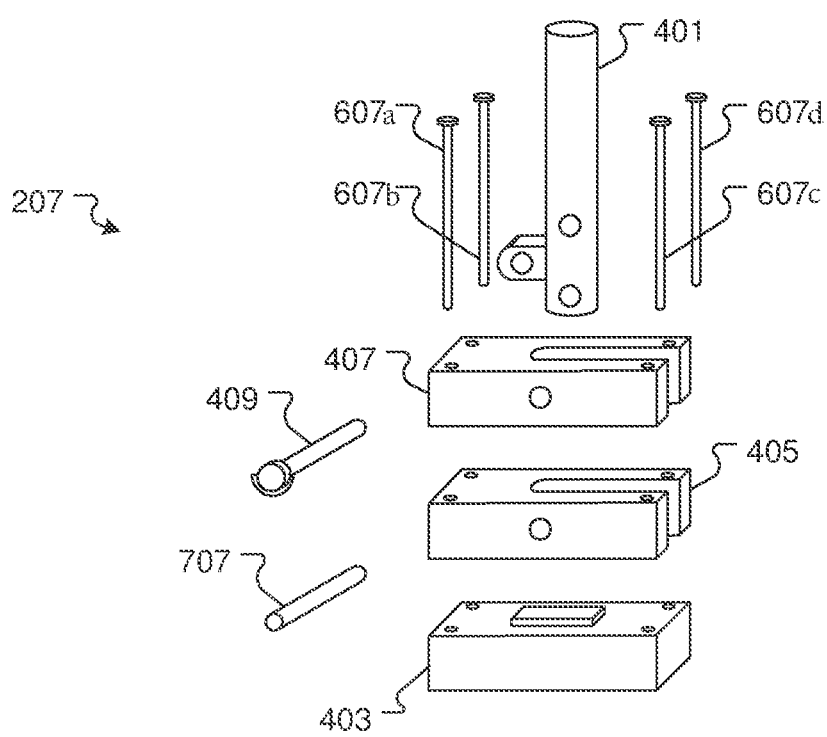
FIG. 11 is an exploded view of the ankle joint of FIG. 4.

Referring now to FIG. 11, the mating foot 403, pin plate 405, and rotation plate 407 of ankle joint 207 are fixedly attached via fasteners 607a-d. Pin 409 is inserted in position hole 903 and one of the positioning holes 505, 507 of pylon 401 that will determine the angle of the prosthetic foot 209 with respect to the prosthetic leg 203

Figure 12:
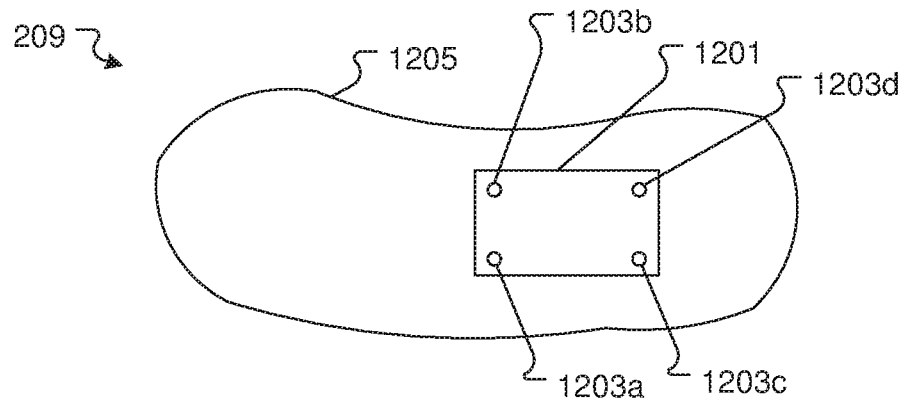
FIG. 12 is a top view of the prosthetic foot of FIGS. 2A and 2B.

Referring now to FIG. 12, prosthetic foot 209 includes a mounting plate 1201 with a plurality of threaded holes 1203a-d to receive fasteners 607a-d from ankle joint 207 to fixedly attached prosthetic foot 209 to ankle joint 207. A functional body 1205 rigidly attached to mounting plate 1201 and replicates the function of a foot.

During use, a position hole 227, 229 is selected and retention pin 409 is inserted locking prosthetic foot 209 in the position for the selected activity, swimming or walking. As needed the position is changed by removing the pin 409 and rotating the prosthetic foot 209 to the new position and reinserting the pin 409.

It should be appreciated that one of the unique features believed characteristic of the present application is that position holes 227 and 229 of pylon 401 enable a user to use the same system 201 for two purposes, walking and swimming. It will be appreciated that the simple method of changing from the walking position to the swimming position enables the user to quickly transition between the two activities. It will also be appreciated that the simple method of changing position facilitates the manufacture of the system and thus enables more users to afford the system 201.

Figure 13:
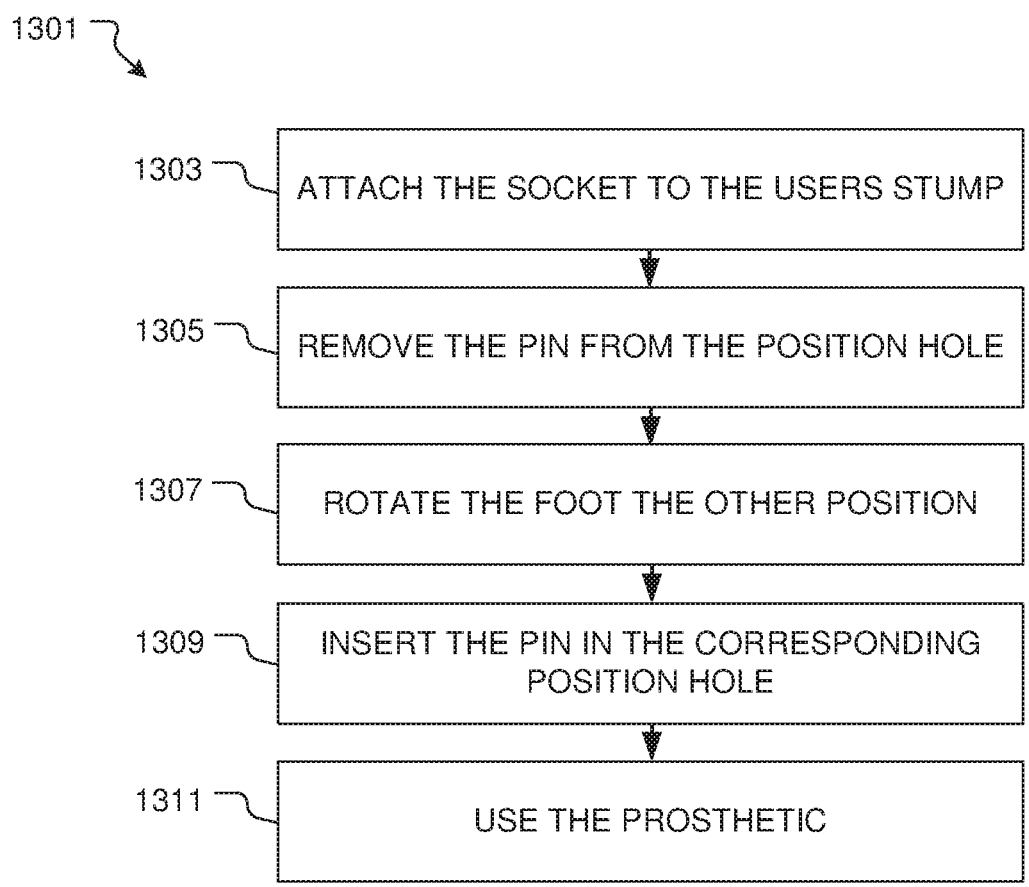
FIG. 13 is a flowchart of the preferred method of use of the system of FIGS. 2A and 2B.

Referring now to FIG. 13 the preferred method of use of system 201 is depicted. Method 1301 includes attaching the socket to the users stump 1303, removing the pin from the position hole 1305, rotating the foot to the other position 1307, inserting the pin in the corresponding position hole 1309 and using the prosthetic 1311.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed:

1. A dual purpose prosthetic foot system comprising:
    an ankle joint having:
    a pylon having:
        a tubular body having an outer surface and sized to loosely fit in a cavity of a prosthetic foot;
        two positioning holes integral to the tubular body; and
        a rotation hole integral to the tubular body that is located at the center of rotation for the positioning holes;
    a pin plate having:
        a first body having a bottom surface and a plurality of holes; a pin hole integral to and passing through the first body;
        a recess on the bottom surface that accommodates a wear plate;
        a first slot integral to the first body and sized to allow the pylon to pass through; and
        a press fit pin that is forced in the pin hole and passes through the rotational hole of the pylon to rotationally attach the pylon to the pin plate;
    a rotation plate having:
        a second body having a plurality of holes;
        a position hole that is integral to and passing through the second body; and
        a second slot that provides the pylon with a freedom of motion; and
        a pin that will be inserted in the positioning hole of the rotation plate having:
        a hollow rod housing a retention device;

a head rigidly attached to the hollow rod
two opposing holes integral to the head; and
a handle with a first and second end that fit in the opposing holes of the head;
wherein the pylon is rotated with respect to the rotation plate alternating between a first position of generally ninety degrees with respect to the rotation plate and a second position of generally 115 to 180 degrees with respect to the rotation plate.

2. The ankle joint of claim 1 wherein the ankle joint has a mating foot having:
a mating body having a plurality of holes;
the wear plate is rigidly attached to the mating body; and
a plurality of fasteners that are sized to fit and interact with the plurality of holes;
wherein the wear plate prevents damage to the pylon of the ankle joint.

3. The dual purpose prosthetic foot system of claim 1 wherein the ankle joint is rigidly attached to a prosthetic leg having:
a leg body having a top end and a bottom end;
a socket for attaching to the user's body integral to and extending inward from the top end;
a cavity for attaching to the ankle joint extending inward from the bottom end; a threaded hole that penetrates the leg body to the cavity; and
a bolt in threaded communication with threaded hole.

4. The dual purpose prosthetic foot system of claim 1 wherein the ankle joint is rigidly attached to a prosthetic foot having:
a mating plate having a plurality of holes; and
a functional body rigidly attached to the mating plate that replicates the function of a foot.

* * * * *